United States Patent
Wang

(10) Patent No.: US 11,052,167 B1
(45) Date of Patent: Jul. 6, 2021

(54) GLASS AROMA DIFFUSER

(71) Applicant: ShenZhen ChangLin Houseware Co., Ltd., Shenzhen (CN)

(72) Inventor: Wen Wang, Shenzhen (CN)

(*) Notice: Subject to any disclaimer, the term of this patent is extended or adjusted under 35 U.S.C. 154(b) by 0 days.

(21) Appl. No.: 17/002,750

(22) Filed: Aug. 25, 2020

(51) Int. Cl.
*A61L 9/14* (2006.01)
*B05B 17/00* (2006.01)

(52) U.S. Cl.
CPC ........... *A61L 9/14* (2013.01); *A61L 2209/134* (2013.01); *B05B 17/0646* (2013.01)

(58) Field of Classification Search
None
See application file for complete search history.

(56) References Cited

U.S. PATENT DOCUMENTS

2018/0193867 A1* 7/2018 Osborn ................. A61L 9/14

OTHER PUBLICATIONS

Amazon.com—500ml Essential Oil Diffuser 3D Glass Aromatherapy Ultrasonic Humidifier Auto Shut-Off, Timer Setting, BPA Free for Home, Hotel, Yoga, Spa Gift [online sale] [retr. Apr. 5, 2021]. https://www.amazon.com/Essential-Diffuser-Aromatherapy-Ultrasonic-Humidifier/dp/B07KQRTVKL/ref=sr_1_3?dchild=1&m= (Year: 2019) A128IXGTF9ON1Q&qid=1617637362&s=merchant-items&sr=1-3&th=1 (Year: 2019).*
YouTube.com—500ml Essential Oil Diffuser 3D Glass Aromatherapy Ultrasonic Humidifer. [online] [retrieved on Apr. 5, 2021]. https://www.youtube.com/watch?v=vhgEGeRx3Ns (Year: 2020).*
Ultra—YouTube.com—Ultrasonic Humidifier Firework 3D Glass Essential Oil Aroma Diffuser 100ml—[online] [retrieved on Apr. 5, 2021]. https://www.youtube.com/watch?v=qB8Jz6wWy5l (Year: 2018).*

* cited by examiner

*Primary Examiner* — Jelitza M Perez
(74) *Attorney, Agent, or Firm* — ZANIP

(57) ABSTRACT

A glass aroma diffuser is provided, including a base, a water tank and a top cover. The bottom of the water tank is fixed on the base, the opening of the water tank is upward, and the bottom of the water tank is provided with an atomizer, and the water tank is configured to carry the liquid to be atomized; the top cover is provided with an exhaust nozzle for discharging mist. The top cover and the water tank of the aroma diffuser of the present disclosure are made of glass material, the atomizer is arranged under the water tank, and the exhaust nozzle is arranged on the top cover, which greatly reduces the use of plastic materials, thus reducing the plastic taste carried in the mist, reducing the probability of mist affecting human health, greatly improving the use experience, and making users feel more comfortable to use.

14 Claims, 8 Drawing Sheets

GLASS AROMA DIFFUSER

TECHNICAL FIELD

The present disclosure relates to an aroma diffuser, in particular to a glass aroma diffuser.

BACKGROUND

Aroma diffuser is a kind of appliance that decomposes water molecules and dissolved plant essential oil into nano scale cold mist by high-frequency vibration generated by ultrasonic vibration equipment, which is distributed in the surrounding air and fills the air with fragrance. The aroma industry has a long history of development. After years of air quality concept popularization, product development and market cultivation, the function and role of aroma diffuser are gradually accepted by the public.

In modern life, the use of air conditioning is more and more frequent. However, the room has been kept closed when the air conditioning is used, which will produce some unpleasant smell. At this time, the aroma diffuser can be use to improve the indoor air odor, so as to keep the indoor air fresh. However, in the actual use, due to the internal structure of the aroma diffuser is generally made of high molecular plastic material, and the core component water tank is made of plastic like PP or ABS, which not only leads to the heavy plastic smell in the sprayed mist, but also the mixture of essential oil and water is in contact with the plastic for a long time, it is difficult to avoid some harmful substances, which may affect human health. In view of above, improvement is required.

SUMMARY

The objective of the present disclosure is to overcome the above defects of the prior art by providing a glass aroma diffuser, which uses glass material instead of plastic material, so as to reduce the smell of plastic carried in the mist, and reduce the possibility of the mist affecting human health.

In order to achieve the above objective, the technical solution provided by the present disclosure is shown as following: A glass aroma diffuser, including a base, a water tank and a top cover, a bottom of the water tank is fixed on the base, an opening of the water tank is upward, the bottom of the water tank is provided with an atomizer, and the water tank is used to carry liquid to be atomized; the top cover is provided with an exhaust nozzle for discharging mist, the top cover and the base surround the whole water tank, the water tank and the top cover are both made of glass material in integrity.

The exhaust nozzle is arranged in a middle position of a top of the top cover, and an inner diameter of the exhaust nozzle gradually decreases from bottom to top.

The base is provided with at least one fan, the fan is configured to blow gas into the aroma diffuser, the gas blown in by the fan flows through a gap between an outer wall of the water tank and the base and a gap between the water tank and the top cover, and the gas blown in by the fan enters the water tank to mix with the mist in the water tank and is discharged from the exhaust nozzle.

The base is provided with a horizontal partition plate, the partition plate is configured to support the water tank, a first air chamber is arranged under the partition plate, an outer edge of the partition plate is provided with a second air chamber, the first air chamber is set right above the fan, the first air chamber is communicated with the second air chamber, and the second air chamber is communicated with a gap between an outer wall of the water tank and the base, the gas blown in by the fan passes through the first air chamber and the second air chamber in sequence.

The space under the partition plate is enclosed to form the first air chamber through an enclosure plate, an outer side of the enclosure plate is provided with a vertical side groove, an inside of the vertical side groove is the second air chamber, the bottom of the water tank is provided with a bottom ring which protrudes horizontally and outwards along a periphery, the bottom ring is provided with a notch, and the vertical side groove is inserted into the notch.

An outer surface of the water tank is sleeved with a sealing strip, the sealing strip is provided with an opening position, the opening position of the sealing strip corresponds to the notch of the bottom ring of the water tank, the opening position of the sealing strip is a gap between the outer wall of the water tank and the base; the bottom of the water tank is placed in the opening of the base, and the sealing strip is configured for sealing between the outer wall of the water tank and the opening of the base.

A periphery of the sealing strip is provided with an annular groove, the opening of the base is inserted into the annular groove of the sealing strip, and the sealing strip is clamped by the opening of the base and the outer wall of the water tank at the same time.

The base includes a bottom plate and a bottom cylinder, the opening of the base is an upper opening of the bottom cylinder, the bottom plate is fixed at an lower opening of the bottom cylinder, the bottom plate supports the partition plate, and the sealing strip and the bottom ring of the water tank are synchronously clamped by the partition plate and the opening of the base.

The upper portion of the sealing strip is provided with an outward extending side wing, and the inner wall of the top cover squeezes the side wing, so that the upper portion of the sealing strip are clamped by the inner wall of the top cover and the outer wall of the water tank.

The bottom of the water tank is provided with a groove surrounding the notch at the position corresponding to the notch, and the groove is configured to collect water returned and condensed by mist from the notch.

The partition plate is provided with an avoidance opening corresponding to the groove, and the water collected in the groove drips from the avoidance opening.

The top cover is provided with an air guide cover, the air guide cover includes an annular portion and a cylindrical portion, an outer edge of the annular portion is connected to the inner wall of the top cover, an inner edge of the annular portion is connected to an outer edge of a top of the cylindrical portion, the cylindrical portion is inserted into the water tank, a ventilation gap is provided between the inner wall of the top cover and the outer wall of the water tank, and a ventilation gap is provided between the cylindrical portion and the top of the water tank, and a ventilation gap is provided between the cylindrical portion and the inner wall of the water tank, and the lowest height of the cylindrical portion is higher than the maximum liquid level height of the water tank. The air guide cover is integrated with the top cover.

An inner wall of the top cover is provided with an exhaust funnel at a position corresponding to the exhaust nozzle, the exhaust funnel is divided into a vertical cylinder connected with an inner wall of the exhaust nozzle and an inclined cylinder connected with the vertical cylinder; an opening of the inclined cylinder faces toward an inner wall of the air guide cover, and an axial direction of the inclined cylinder forms a non right angle with an axial direction of the vertical cylinder.

The base is provided with the horizontal partition plate, the partition plate is configured to support the water tank, the middle of the bottom of the water tank is provided with a through hole, a ring-shaped sealing body is provided at a position of the partition plate corresponding to the through hole, the atomizer is embedded inside the sealing body, and a diameter of the sealing body is larger than that of the through hole, the sealing body abuts against the bottom of the water tank and the sealing body is clamped by the partition plate and the water tank, and the liquid in the water tank flows to the atomizer through the through hole.

A height of an inner bottom surface of the water tank gradually decreases from the periphery to the middle position, while a height of the through hole toward the outer edge of the water tank is lowest.

The partition plate is provided with a holding groove at a middle position, the sealing body is placed in the holding groove, and the sealing body and the holding groove are in a tight fit.

Compared with the prior art, the present disclosure has the following advantageous effect: both the top cover and the water tank are made of glass material, the atomizer is arranged under the water tank, and the exhaust nozzle is arranged on the top cover, which greatly reduces the use of plastic materials, thus reducing the plastic taste carried in the mist, reducing the probability of mist affecting human health, greatly improving the use experience, and making users feel more comfortable to use.

Figure 1:
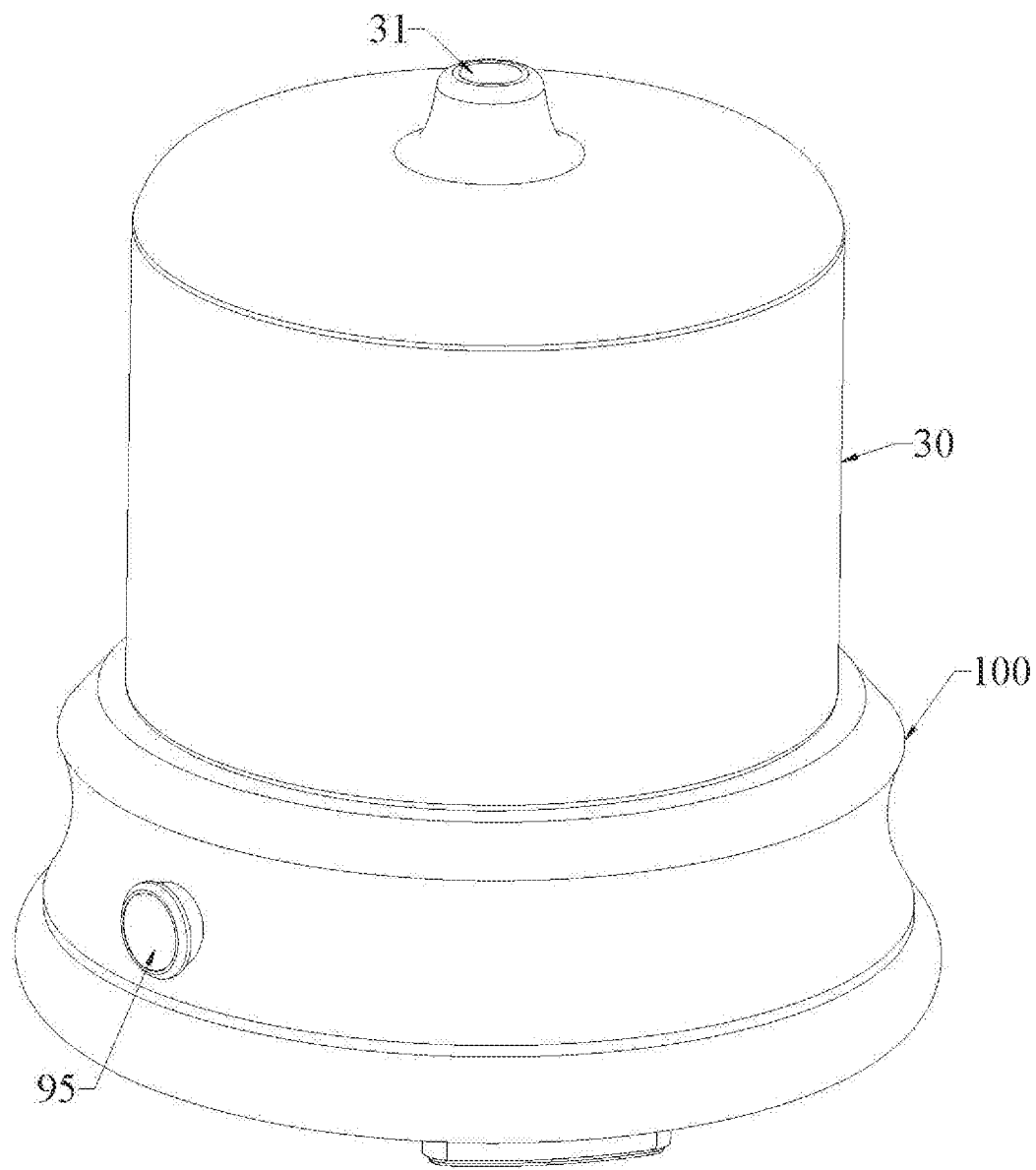
FIG. 1 and FIG. 2 are perspective views showing of the aroma diffuser of the present disclosure

It should be noted that the products shown in the above views are properly reduced or enlarged to fit the size of the drawing and show the view clear, and there is no restriction on the size of the products shown in the view.

DETAILED DESCRIPTION OF THE EMBODIMENTS

In order to fully understand the technical content of the present disclosure, the technical solution of the present disclosure is further introduced and illustrated in combination with specific embodiments.

The embodiment provided by the present disclosure is an aroma diffuser, and the specific structure is shown in FIGS. 1-8.

As shown in FIG. 1, the aroma diffuser of the present embodiment includes a base 100 and a top cover 30. The top cover 30 is provided with an exhaust nozzle 31 for discharging mist. A switch button 95 is set on the side of the base 100, which is used to control the power on or off of the aroma device. In other embodiments, the switch button can also be used to control the working gear of the aroma diffuser. The switch button can also be replaced by a rotary switch.

Figure 2:
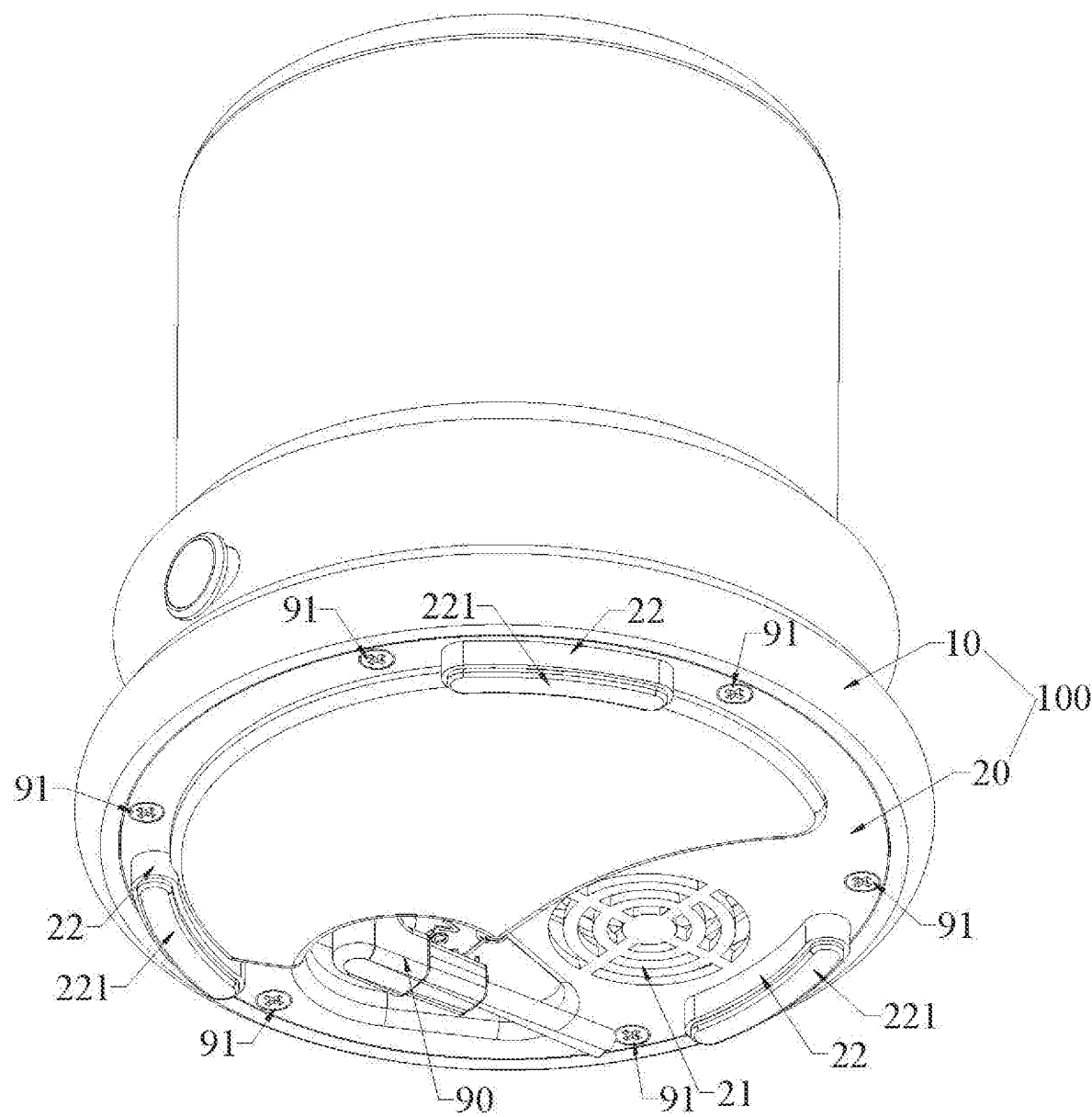

As shown in FIG. 2, the base 100 includes a bottom plate 20 and a bottom cylinder 10. The bottom cylinder 10 may be made of wood. The bottom plate 20 is fixed at the lower opening of the bottom cylinder 10 by six screws 91. The bottom plate 20 serves as the bottom support of the whole aroma diffuser. The bottom surface of the bottom plate 20 is provided with three arc-shaped support feet 22 which are evenly distributed, and the buffer rubber block 221 is fixed at the support foot 22. The power plug 90 can also be inserted under the bottom plate 20. An air intake grid 21 is arranged on the bottom plate 20.

Figure 3:
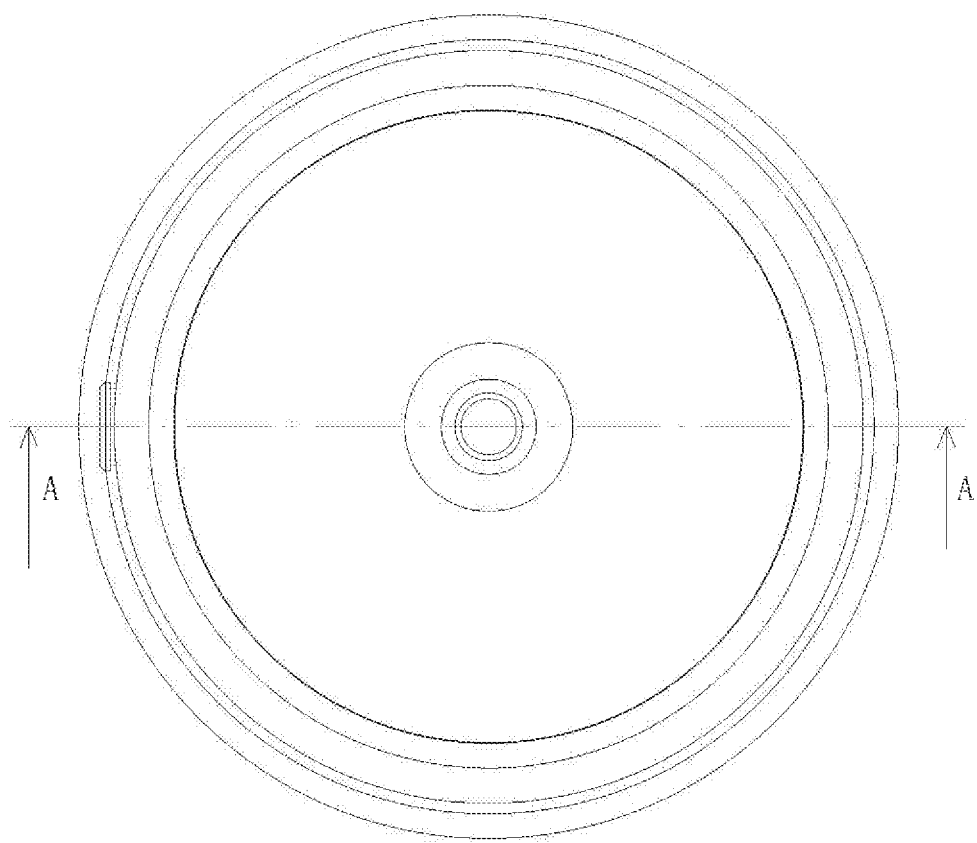
FIG. 3 is a top view of the aroma diffuser of the present disclosure.
Figure 4:
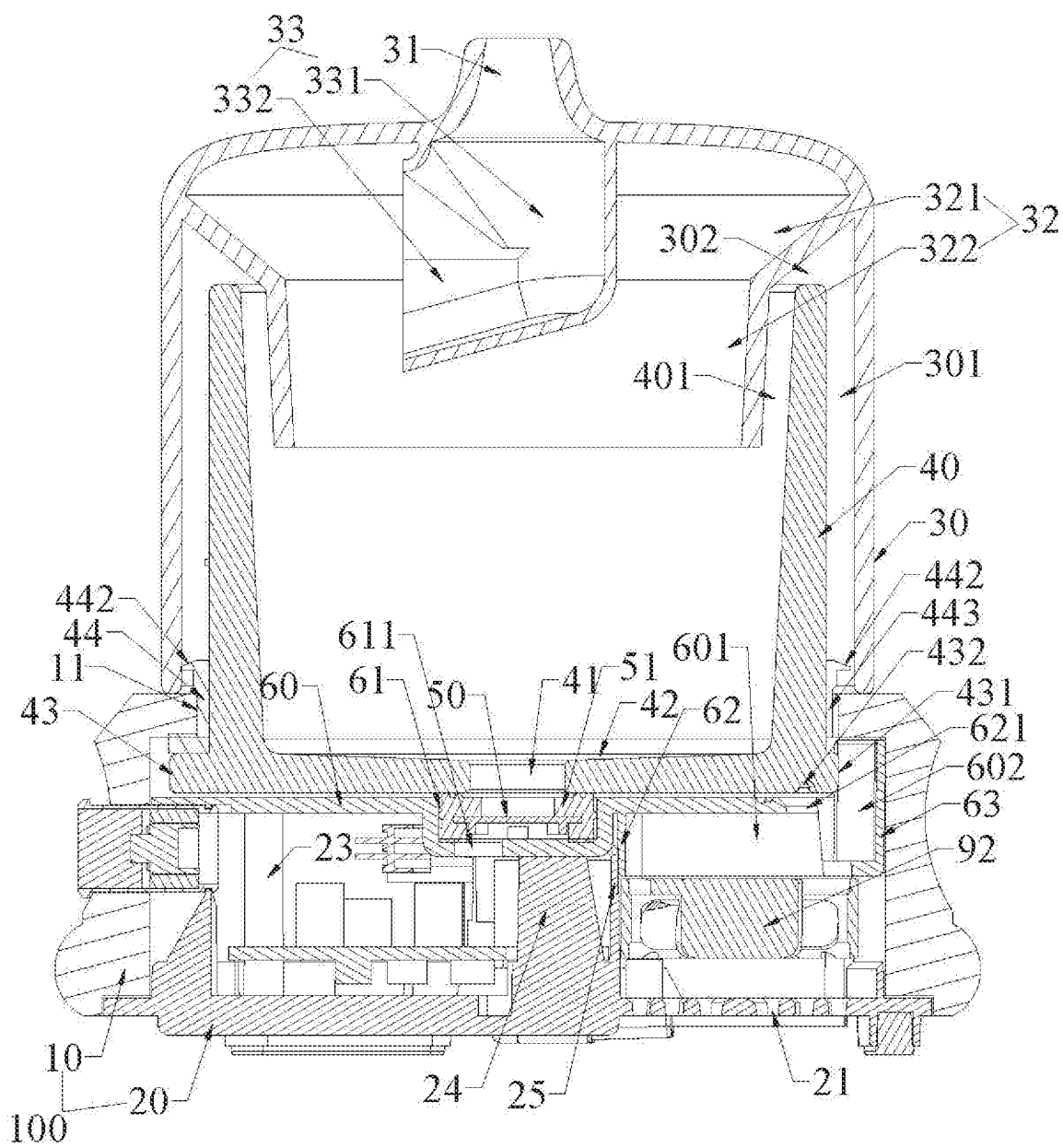
FIG. 4 is a sectional view of section A-A in FIG. 3.

The sectional view as shown in FIG. 4 is obtained by sectioning the whole aroma diffuser shown in FIG. 3 along the A-A section.

Figure 5:
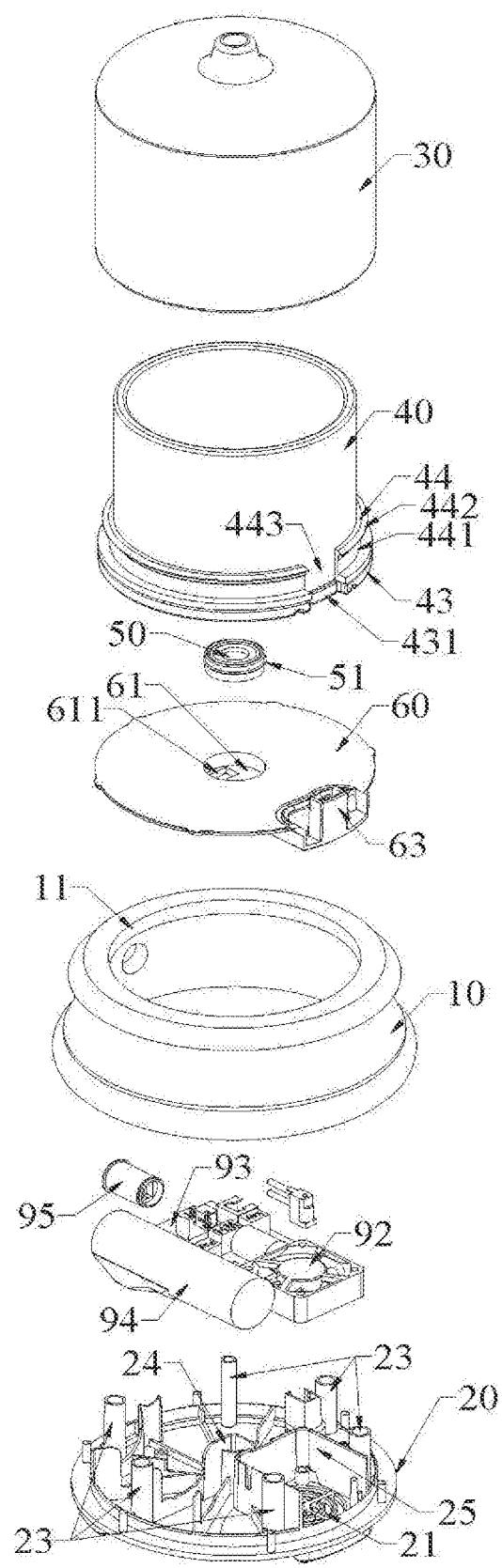
FIG. 5 is an exploded view of the aroma diffuser of the present disclosure.
Figure 6:
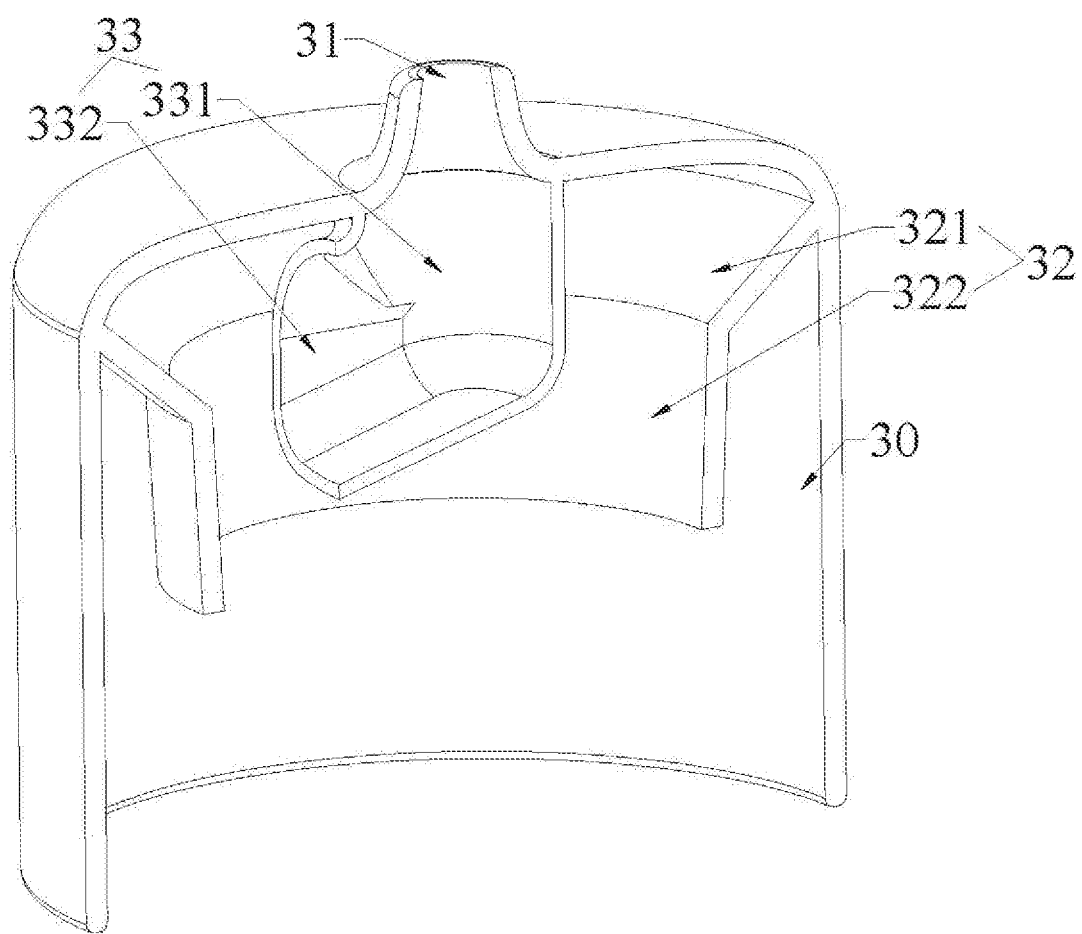
FIG. 6 is a sectional perspective view showing of the top cover of the aroma diffuser of the present disclosure.

As shown in FIG. 4 and FIG. 5, the aroma diffuser further includes a water tank 40. The bottom of the water tank 40 is fixed on the base 100, and the water tank 40 is configured to carry the liquid to be atomized. The lower edge of the top cover 30 is attached to the top surface of the bottom cylinder 10. The top cover 30 and the base 100 surround the whole water tank 40. In the present embodiment, the water tank 40 and the top cover 30 are all made of glass in integrity. The opening of the water tank 40 is upward, and the bottom of the water tank 40 is provided with an atomizer 50.

referring to FIG. 4 and FIG. 6, the internal specific structure of the top cover 30 can be seen. An air guide cover 32 is arranged in the top cover 30, and the air guide cover 32 is integrated with the top cover 30. The air guide cover 32 includes an annular portion 321 and a cylindrical portion 322. The outer edge of the annular portion 321 is connected to the inner wall of the top cover 30, and the inner edge of the annular portion 321 is connected to the outer edge of the top of the cylindrical portion 322. The cylindrical portion 322 is inserted into the water tank 40, and when in use, the height of the cylindrical portion 322 at the lowest position is higher than the maximum liquid level height of the water tank 40. There is a ventilation gap 301 between the inner wall of the top cover 30 and the outer wall of the water tank 40, a ventilation gap 302 between the annular portion 321 and the top of the water tank 40, and a ventilation gap 401 between the cylindrical portion 322 and the inner wall of the water tank 40.

As shown in FIG. 4 and FIG. 6, the exhaust nozzle 31 is located in the middle position of the top of the top cover 30, and the inner diameter of the exhaust nozzle 31 gradually decreases from bottom to top. The inner wall of the top cover 30 is provided with an exhaust funnel 33 at the position corresponding to the exhaust nozzle 31. The exhaust funnel 33 is divided into a vertical cylinder 331 connected to the inner wall of the exhaust nozzle 31 and an inclined cylinder 332 connected to the vertical cylinder 331. The opening of the inclined cylinder 332 is toward the inner wall of the air guide cover 32, and the axial direction of the inclined cylinder 332 forms a non right angle with the axial direction of the vertical cylinder 331.

As shown in FIG. 4, the air flow blown into the water tank 40 by the base 100 will pass through the ventilation gap 301, the ventilation gap 302 and the ventilation gap 401 in sequence, and then reaching the place between the cylinder portion 322 and the liquid level of the water tank 40 to mix with the mist generated by the atomizer 50. The mixed gas then flows upward into the cylindrical portion 322, and then passes through the inclined cylinder 332 and the vertical cylinder 331 in sequence, and finally exhausts from the exhaust nozzle 31.

As shown in FIG. 4 and FIG. 5, the opening of the base 100 is the upper opening 11 of the bottom cylinder 10, and a horizontal partition plate 60 is arranged in the bottom cylinder 10. The partition plate 60 is configured to support the water tank 40. The lower portion of the water tank 40 passes through the opening 11 of the bottom cylinder 10, and then the bottom surface of the water tank 40 is in contact with the surface of the partition plate 60. A through hole 41 (as shown in FIG. 4) is arranged in the middle of the bottom of the water tank 40, and a ring-shaped elastic sealing body 51 is arranged at the position of the partition plate 60 corresponding to the through hole 41. The atomizer 50 is embedded inside the sealing body 51, and the atomizer 50 of the present embodiment adopts a plate-like atomizing piece. The diameter of the sealing body 51 is larger than that of the through hole 41, the sealing body 51 abuts against the bottom of the water tank 40, and the partition plate 60 and the bottom surface of the water tank 40 clamp the sealing body 51 tightly to avoid the liquid flowing out of the sealing body 51. As shown in FIG. 4 and FIG. 5, the partition plate 60 is provided with a holding groove 61 at the middle position, the sealing body 51 is placed in the holding groove 61, and a square hole 611 for the wiring harness to pass through is also arranged on the bottom surface of the holding groove 61. The sealing body 51 and the holding groove 61 are in a tight fit. The liquid in the water tank 40 flows through the through hole 41 to the atomizer 50. In the present embodiment, as shown in FIG. 4, the height of the bottom surface 42 inside the water tank 40 gradually decreases from the periphery to the middle, and the outer edge of the through hole 41 faces toward of the interior of the water tank 40 is at the lowest height, so that the liquid can flow directly into the through hole 41 even when there is less water at the bottom of the water tank 40.

As shown in FIG. 4 and FIG. 5, the bottom plate 20 is provided with a top pillar 23 distributed around and a top plate 24 in the middle, which are used to support the whole partition plate 60. A fan 92 is arranged between the bottom plate 20 and the partition plate 60. The fan 92 is configured to blow external gas into the aroma diffuser. The air intake grid 21 on the bottom plate 20 is the air inlet of fan 92. The bottom plate 20 is provided with fences 25 on three sides at the position of the air intake grid 21, and the fan 92 is fixed in the fences 25. The first air chamber 601 is arranged under the partition plate 60, and the second air chamber 602 is arranged at the outer edge of the division plate 60. Specifically, in the present embodiment, referring to FIG. 4 and FIG. 8, the space under the partition plate 60 is enclosed by the enclosure plate 62 to form the first air chamber 601, the outer side of the enclosure plate 62 is provided with a vertical side groove 63, and the interior of the vertical side groove 63 is the second air chamber 602. As shown in FIG. 4, the enclosure plate 62 is also inserted into the fence 25 and is close to the inner wall of the fence 25. The first air chamber 601 is located directly above the fan 92, and the first air chamber 601 is communicated with the second air chamber 602. The second air chamber 602 is communicated with the gap between the outer wall of the water tank 40 and the opening 11 on the bottom cylinder 10. As shown in FIG. 4 and FIG. 5, the bottom of the water tank 40 is provided with a bottom ring 43 which protrudes horizontally and outwards along the periphery. The bottom ring 43 is provided with a notch 431, and the side groove 63 is inserted into the notch 431. An elastic sealing strip 44 is sleeved on the outer surface of the water tank 40. The sealing strip 44 is provided with an opening position 443. And the opening position 443 of the sealing strip 44 corresponds to the position of the notch 431 of the bottom ring 43 of the water tank 40. Since the bottom of the water tank 40 is placed in the upper opening 11 of the bottom cylinder 10, the sealing strip 44 is used for sealing between the outer wall of the water tank 40 and the upper opening 11 of the bottom cylinder 10, and the opening position 443 of the sealing strip 44 is the gap between the outer wall of the water tank 40 and the opening 11 on the bottom cylinder 10. Specifically, the periphery of the sealing strip 44 is provided with an annular groove 441. The upper opening 11 of the bottom cylinder 10 is inserted into the annular groove 441 of the sealing strip 44, so that in the horizontal direction, the sealing strip 44 is clamped by the upper opening 11 of the bottom cylinder 10 and the outer wall of the water tank 40 at the same time, while in the vertical direction, the sealing strip 44 and the bottom ring 43 of the water tank 40 are clamped synchronously by the partition plate 60 and the upper opening 11 of the bottom cylinder 10. The upper portion of the sealing strip 44 is provided with an annular side wing 442 extending outwards. When the top cover 30 covers the whole water tank 40, the inner wall of the top cover 30 will squeeze the side wing 442. Therefore, the upper portion of the sealing strip 44 is clamped tightly by the inner wall of the top cover 30 and the outer wall of the water tank 40, so as to avoid air leakage at the position except the opening position 443 of the sealing strip 44.

Figure 7:
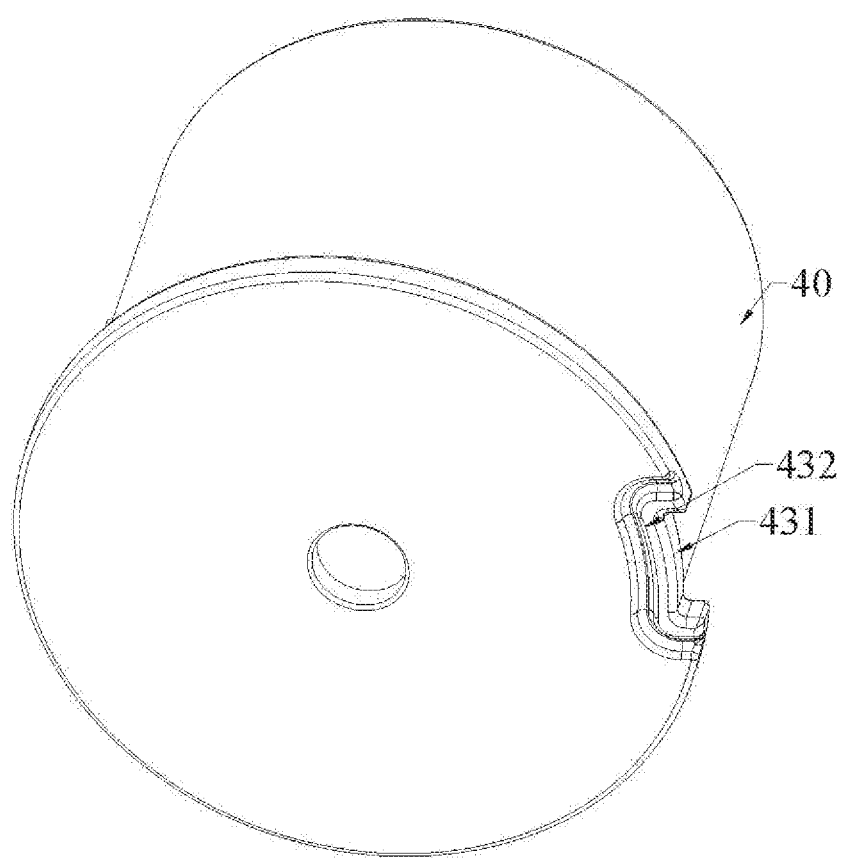
FIG. 7 is a perspective view showing of the bottom of the water tank of the aroma diffuser of the present disclosure.
Figure 8:
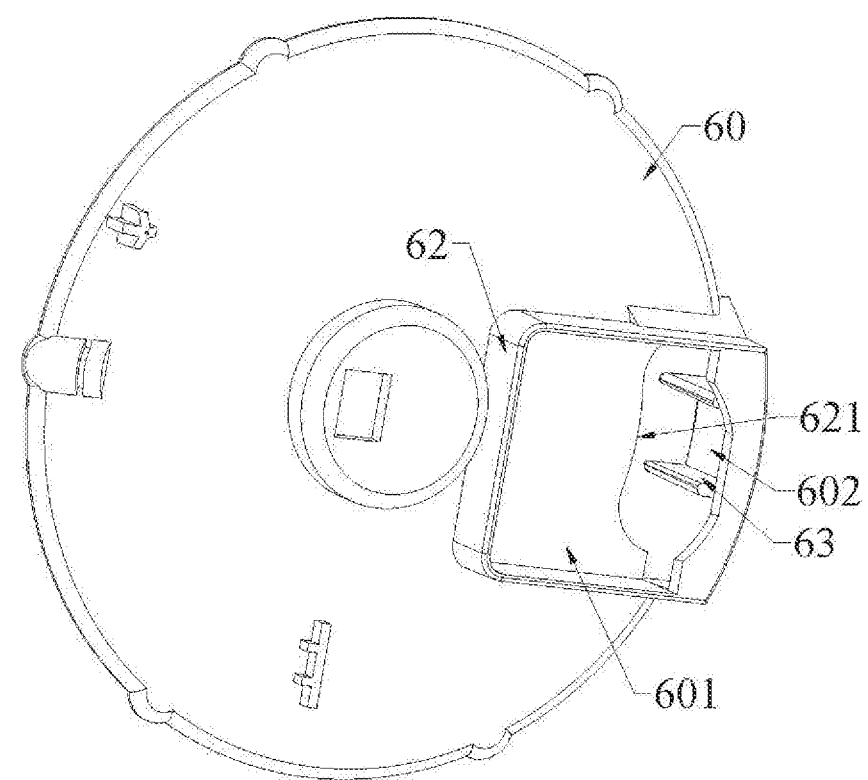
FIG. 8 is a perspective view showing of the bottom of the partition plate of the aroma diffuser of the present disclosure.

In addition, referring to FIG. 4 and FIG. 7, the bottom surface of water tank 40 is provided with a groove 432 surrounding the notch 431 at the position corresponding to the notch 431. The groove 432 is configured to collect the water returned and condensed by the mist which flows from the notch 431 to prevent the condensed water from spreading to other places on the bottom of the water tank 40. As shown in FIG. 4 and FIG. 8, the partition plate 60 is provided with an avoidance opening 621 corresponding to the groove 432 as shown in FIG. 7, so that the water collected by the groove 432 will drip from the avoidance opening 621 under the action of gravity.

Besides, as shown in FIG. 5, a battery 94 and a circuit board 93 are arranged between the partition plate 60 and the bottom plate 20. The circuit board 93 is electrically connected with the battery 94, the switch button 95, the fan 92 and the atomizer 50, respectively. The battery 94 is configured to provide power for the entire aroma diffuser.

When using the aroma diffuser, the fan 92 is turned on by the switch button 95, and the fan 92 starts to work. The gas blown in by the fan 92 passes through the first air chamber 601 and the second air chamber 602 in sequence, and then flows through the gap between the outer wall of the water tank 40 and the opening 11 of the bottom cylinder 10 (i.e., the opening position 443 of the sealing strip 44), the ventilation gap 301 between the outer wall of the water tank 40 and the inner wall of the top cover 30, the ventilation gap 302 between the annular portion 321 and the top of the water tank 40, the ventilation gap 401 between the cylindrical portion 322 and the inner wall of the water tank 40, and then reaches to the space between the cylindrical portion 322 and the liquid level of the water tank 40, so as to mix with the mist generated by the atomizer 50 to form a mixed gas. The mixed gas then flows upward into the cylindrical portion 322, and then passes through the inclined cylinder 332 and the vertical cylinder 331 in sequence, and finally being discharged from the exhaust nozzle 31.

The top cover 30 and the water tank 40 of the aroma diffuser provided by the present disclosure are made of glass material, the atomizer 50 is arranged under the water tank 40, and the exhaust nozzle 31 is arranged on the top cover 30, which greatly reduces the use of plastic materials, thus reducing the plastic taste carried in the mist, reducing the probability of mist affecting human health, greatly improving the use experience, and making users feel more comfortable to use.

In the description of the present disclosure, it should be noted that the orientation or position relationship indicated by the terms "up", "down", "top" and "bottom" is based on the orientation or position relationship shown in the drawings, which is only for the convenience of describing the present disclosure and simplifying the description, but not indicating or implying that the device or element referred to must have a specific orientation, or be constructed and operated in a specific orientation. It cannot be understood as a limitation of the present disclosure. In addition, the terms "first" and "second" are only used for description purpose and cannot be understood to indicate or imply relative importance.

The above description only further illustrates the technical content of the present disclosure by means of embodiments, so as to facilitate readers to understand it more easily, but it does not mean that the implementation mode of the present disclosure is limited to this. Any technical extension or recreation made according to the present disclosure is protected by the present disclosure.

What is claimed is:

1. A glass aroma diffuser, comprising a base, a water tank and a top cover; a bottom of the water tank is fixed on the base, an opening of the water tank is upward, the bottom of the water tank is provided with an atomizer, and the water tank is used to carry liquid to be atomized; the top cover is provided with an exhaust nozzle for discharging mist, the top cover and the base surround the whole water tank, the water tank and the top cover are both made of glass material in integrity;

the base is provided with at least one fan, the fan is configured to blow gas into the aroma diffuser, the gas blown in by the fan flows through a gap between an outer wall of the water tank and the base and a gap between the water tank and the top cover, and the gas blown in by the fan enters the water tank to mix with mist in the water tank and is discharged from the exhaust nozzle;

the base is provided with a horizontal partition plate, the horizontal partition plate is configured to support the water tank, a first air chamber is arranged under the horizontal partition plate, an outer edge of the horizontal partition plate is provided with a second air chamber, the first air chamber is set right above the fan, the first air chamber is communicated with the second air chamber, and the second air chamber is communicated with the gap between the outer wall of the water tank and the base, the gas blown in by the fan passes through the first air chamber and the second air chamber in sequence; and space under the horizontal partition plate is enclosed to form the first air chamber through an enclosure plate, an outer side of the enclosure plate is provided with a vertical side groove, an inside of the vertical side groove is the second air chamber, the bottom of the water tank is provided with a bottom ring which protrudes horizontally and outwards along a periphery, the bottom ring is provided with a notch, and the vertical side groove is inserted into the notch.

2. The glass aroma diffuser according to claim 1, wherein the exhaust nozzle is arranged in a middle position of a top of the top cover, and an inner diameter of the exhaust nozzle gradually decreases from bottom to top.

3. The glass aroma diffuser according to claim 1, wherein an outer surface of the water tank is sleeved with a sealing strip, the sealing strip is provided with an opening position, the opening position of the sealing strip corresponds to the notch of the bottom ring of the water tank, the opening position of the sealing strip is the gap between the outer wall of the water tank and the base; the bottom of the water tank is placed in the opening of the base, and the sealing strip is configured for sealing between the outer wall of the water tank and the opening of the base.

4. The glass aroma diffuser according to claim 3, wherein a periphery of the sealing strip is provided with an annular groove, the opening of the base is inserted into the annular groove of the sealing strip, and the sealing strip is clamped by the opening of the base and the outer wall of the water tank at the same time.

5. The glass aroma diffuser according to claim 4, wherein the base comprises a bottom plate and a bottom cylinder, the opening of the base is an upper opening of the bottom cylinder, the bottom plate is fixed at an lower opening of the bottom cylinder, the bottom plate supports the horizontal partition plate, and the sealing strip and the bottom ring of the water tank are synchronously clamped by the horizontal partition plate and the opening of the base.

6. The glass aroma diffuser according to claim 3, wherein an upper portion of the sealing strip is provided with a side wing extending outward, and an inner wall of the top cover squeezes the side wing, so that the upper portion of the sealing strip are clamped by the inner wall of the top cover and the outer wall of the water tank.

7. The glass aroma diffuser according to claim 1, wherein the bottom of the water tank is provided with a groove surrounding the notch at a position corresponding to the notch, and the groove is configured to collect water returned and condensed by mist from the notch.

8. The glass aroma diffuser according to claim 7, wherein the horizontal partition plate is provided with an avoidance opening corresponding to the groove, and the water collected in the groove drips from the avoidance opening.

9. The glass aroma diffuser according to claim 1, wherein the top cover is provided with an air guide cover, the air guide cover comprises an annular portion and a cylindrical portion, an outer edge of the annular portion is connected to an inner wall of the top cover, an inner edge of the annular portion is connected to an outer edge of a top of the cylindrical portion, the cylindrical portion is inserted into the water tank, a ventilation gap is provided between the inner wall of the top cover and an outer wall of the water tank, and a ventilation gap is provided between the cylindrical portion and a top of the water tank, and a ventilation gap is provided between the cylindrical portion and an inner wall of the water tank, and a lowest height of the cylindrical portion is higher than a maximum liquid level height of the water tank.

10. The glass aroma diffuser according to claim 9, wherein the air guide cover and the top cover are formed in integrity.

11. The glass aroma diffuser according to claim 9, wherein the inner wall of the top cover is provided with an exhaust funnel at a position corresponding to the exhaust nozzle, the exhaust funnel is divided into a vertical cylinder connected with an inner wall of the exhaust nozzle and an inclined cylinder connected with the vertical cylinder; an opening of the inclined cylinder faces toward an inner wall of the air guide cover, and an axial direction of the inclined cylinder forms a non right angle with an axial direction of the vertical cylinder.

12. The glass aroma diffuser according to claim 1, wherein, the bottom of the water tank is provided with a through hole, a ring-shaped sealing body is provided at a position of the horizontal partition plate corresponding to the through hole, the atomizer is embedded inside the sealing body, and a diameter of the sealing body is larger than that of the through hole, the sealing body abuts against the bottom of the water tank and the sealing body is clamped by the horizontal partition plate and the water tank, and the liquid in the water tank flows to the atomizer through the through hole.

13. The glass aroma diffuser according to claim 12, wherein a height of an inner bottom surface of the water tank gradually decreases from the periphery to the middle position, while a height of the through hole toward an outer edge of the water tank is smallest.

14. The glass aroma diffuser according to claim 12, wherein the horizontal partition plate is provided with a holding groove at a middle position, the sealing body is placed in the holding groove, and the sealing body and the holding groove are in a tight fit.

\* \* \* \* \*